United States Patent [19]
Voeste et al.

[11] 4,259,536
[45] Mar. 31, 1981

[54] CONTINUOUS PROCESS OF PRODUCING FATTY ALCOHOLS

[75] Inventors: Theodor Voeste; Hans J. Schmidt, both of Frankfurt am Main; Friedemann Marschner, Oberursel, all of Fed. Rep. of Germany

[73] Assignee: Metallgesellschaft Aktiengesellschaft, Frankfurt am Main, Fed. Rep. of Germany

[21] Appl. No.: 100,576

[22] Filed: Dec. 5, 1979

[30] Foreign Application Priority Data

Dec. 14, 1978 [DE] Fed. Rep. of Germany ....... 2853990

[51] Int. Cl.³ ............................................ C07C 29/136
[52] U.S. Cl. .................................... 568/885; 260/690; 422/224
[58] Field of Search ......................... 568/885; 260/690; 422/224

[56] References Cited

U.S. PATENT DOCUMENTS 3,180,898  4/1965  Eisenlohr et al. .................... 568/885

Primary Examiner—Joseph E. Evans
Attorney, Agent, or Firm—Sprung, Felfe, Horn, Lynch & Kramer

[57] ABSTRACT

An improved continuous process of producing fatty alcohols by a catalytic hydrogenation of fatty acids wherein hydrogen is fed and distributed into the annular space through nozzles which are specially designed to effect a pressure loss of 15 to 30 bars is disclosed. Guide tubes having specific dimensions are disposed above said nozzles. The feedstock to be treated and the catalyst dispersion are fed separately. The new process results in milder conditions for the catalyst and in a higher throughput rate.

4 Claims, 1 Drawing Figure

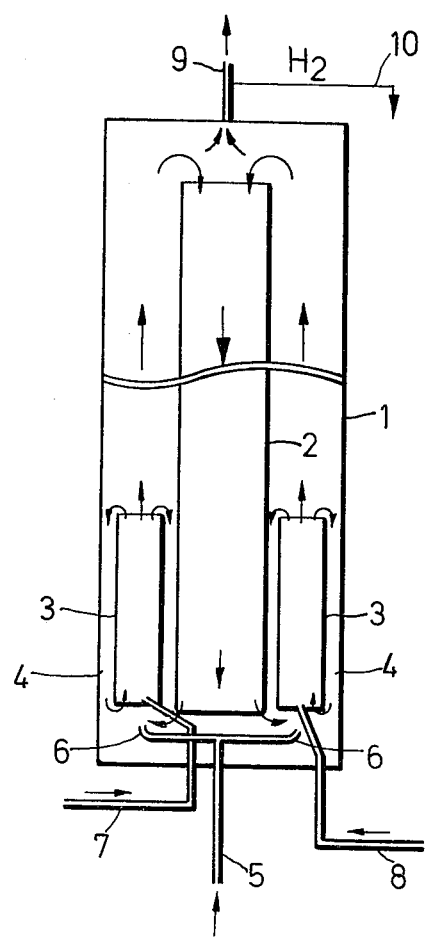

4,259,536

CONTINUOUS PROCESS OF PRODUCING FATTY ALCOHOLS

BACKGROUND OF THE INVENTION

1. Field of the Invention

This invention relates to a continuous process of producing fatty alcohols by a catalytic hydrogenation of fatty acids or fatty acid derivatives at temperatures of 240° to 330° C. and pressures of 200 to 700 bars in the presence of copper-chromium oxide catalysts, which may be modified by additional components, comprising feeding the feedstock to be hydrogenated into a high pressure chamber, feeding hydrogen and feeding a dispersion of the catalyst into said high pressure chamber equipped with a return pipe, thoroughly mixing the ingredients, causing the reaction to take place in the presence of a large quantity of material which has been almost completely or completely reacted, withdrawing the surplus hydrogen and recycling it to the high pressure chamber, and withdrawing the reaction product.

A thorough mixing and an intense exchange of material are desired in such process, also a high yield of hydrogenated product and a useful life of the catalyst which is used.

2. Discussion of the Prior Art

In an attempt to meet these requirements it has been proposed to produce fatty alcohols continuously by a catalytic hydrogenation of fatty acid or fatty acid derivatives at temperatures of 240° to 330° C. and pressures of 200 to 700 bars in the presence of copper-chromium oxide catalysts, which may be modified by additional components, wherein the feedstock to be hydrogenated is continuously fed into a high pressure chamber, in which a large quantity of material which has been almost completely or completely reacted is thoroughly mixed with the catalyst and the hydrogen (German Pat. No. 1,112,056; U.S. Pat. No. 3,180,898).

In the known process, it is usual to carry out the reaction in a high pressure reactor, in which a return pipe for recycling the completely reacted material is disposed suitably in a central position. Hydrogen is fed and distributed at the lower end of the reactor. The hydrogen supplied in a surplus produces a mammoth pump effect, which causes the catalyst-containing fatty alcohol to rise. When the hydrogen has been separated, the fatty alcohol returns through the return pipe into the lower part (section) of the reactor. Generally, the "lower part" is a part from the bottom of the reactor, which is generally vertical and cylindrical, up to a point one-third of the vessel's height, preferably up to no higher from the bottom than one diameter of the vessel. In order to ensure that the mammoth pump action will be as effective as possible, the upper part (section) of the reactor is provided with suitable means for separating the hydrogen as effectively as possible so that the effect of entrained hydrogen bubbles to decrease the velocity of the return flow is minimized. A catalyst, which is usually mixed with fatty alcohol to form a dispersion, is also fed at the required rate into the reactor cycle. The acid is distributed as uniformly as possible at the lower end of the reactor and mixes with the circulating reaction mixture. The ratio of feedstock to circulating reaction mixture should be at least 1:10, preferably 1:100 to 1:1000. The resulting mixing will result in only a slight damage to the catalyst. Because the fatty acid is mixed with virtually completely reacted material and owing to the presence of surplus hydrogen, which is supplied to the high pressure chamber at a rate which is at least 3 times and suitably 10 to 50 times higher than the rate at which hydrogen is consumed, the fatty acid is rapidly diluted and is most effectively esterified with completely reacted material, consisting mainly of fatty alcohol. The resultant fatty acid-fatty alcohol ester does not attack the catalyst and is hydrogenated in the reaction chamber to form fatty alcohol. Surplus hydrogen leaves the reactor at its top jointly with the reacton water, the fatty alcohol and the catalyst at a rate which depends on the feed rates of fatty acid and catalyst dispersion.

It is an object of the invention to improve the mixing of the circulating material with the fatty acid feedstock so that the attack of acid on the catalyst will be further decreased and the catalyst will be damaged less than even in the process described above. Additionally, it is an object to increase the throughput and/or decrease the catalyst consumption.

SUMMARY OF THE INVENTION

This object is accomplished according to the invention that hydrogen is introduced and distributed into the high pressure chamber through 4 to 10 nozzles, which are disposed in the lower part (section) of the annular chamber and are so dimensioned that the pressure loss therein amounts to 5 to 50 bars, preferably 15 to 30 bars, guide tubes are provided above the nozzles and are dimensioned that the total cross-sectional area of these guide tubes amounts to 70 to 150% of the cross-section of the return pipe, the nozzles are disposed centrally under the guide tubes at a distance therefrom which is one-half to twice the diameter of the guide tube, the height of each guide tube is 3 to 10 times, preferably 5 times, the diameter of the guide tube, the lower end of each guide tube is approximately level with the lower end or disposed up to three guide tube diameters above the lower end of the return pipe, and the feedstock to be hydrogenated and the catalyst dispersion are fed above the nozzles employed for hydrogen introduction.

According to a preferred further feature of the invention, the feedstock to be hydrogenated is fed on a level within a range between about one-half guide tube diameter below the lower end of a guide tube and about one guide tube diameter above the lower end of a guide tube and the feedstock is distributed to the several guide tubes.

According to a further preferred feature of the invention, the nozzles for feeding the hydrogen are disposed centrally under respective guide tubes at a distance of one-half to two guide tube diameters.

According to another preferred feature of the invention, the catalyst is fed to a guide tube like the feedstock to be hydrogenated. In that case, no fatty acid is desirably fed to that guide tube or those guide tubes, not exceeding two, in which the catalyst is mixed so that the catalyst can be activated by surplus hydrogen in a state of high turbulence.

The advantages afforded by the invention reside particularly in that a simple and economical process is provided by which fatty acids and their derivatives can be reduced to fatty alcohols. The process is entirely continuous. The catalyst is treated gently and the end product is obtained in a high yield.

Because the hydrogen is distributed by properly designed and arranged nozzles and fed at a high velocity, a thorough mixing of the reactants and an intense mass transfer between them are effected. There will even be a return flow in the annular space outside the guide tubes so that the flow in the guide tubes will be particularly large particularly because the velocity of the reaction material flowing down in the return pipe is not decreased but even increased by the measures which have been described. All measures together result in an instantaneous mixing in a very small space in the presence of highly turbulent hydrogen.

BRIEF DESCRIPTION OF DRAWING

Apparatus suitable for carrying out the process according to the invention is shown diagrammatically and by way of example on the accompanying drawing.

DESCRIPTION OF SPECIFIC EMBODIMENT

Referring to the drawing, there is shown a high pressure chamber 1, a return pipe 2, guide tubes 3, an annular space 4, means 5 for supplying hydrogen, nozzles 6, means 7 for supplying the feedstock to be hydrogenated, means 8 for supplying catalyst dispersion, means 9 for withdrawing hydrogenated product and means 10 for recycling surplus hydrogen.

What is claimed is:

1. In a continuous process of producing fatty alcohols by a catalytic hydrogenation of fatty acids or fatty acid derivatives at a temperature of 240° to 330° C. and pressure of 200 to 700 bars in the presence of a catalyst containing copper-chromium oxide, comprising feeding the feedstock to be hydrogenated into a high pressure chamber equipped with a return pipe, feeding hydrogen and feeding a dispersion of the catalyst into said high pressure chamber, thoroughly mixing the ingredients, causing the reaction to take place in the presence of a large quantity of material which has been almost completely or completely reacted, withdrawing the surplus hydrogen and recycling it to the high pressure chamber, and withdrawing the reaction product, the improvement wherein the reactor is a generally vertically disposed reactor within which sits a generally vertically disposed return pipe surrounded by said high pressure chamber in fluid communication therewith whereby said high pressure chamber is in the form of an annular chamber, hydroden is introduced and distributed into said high pressure chamber through 4 to 10 nozzles disposed in the lower portion of the annular chamber, said nozzles being so dimensioned that the pressure loss upon passage of hydrogen into said annular chamber is 2.5 to 50 bars, said annular chamber contains guide tubes above said nozzles which guide tubes are so dimensioned that the total cross-sectional area of these guide tubes amounts to 70 to 150 percent of the cross-section of said return pipe, said nozzles being centrally disposed under said guide tubes at a distance therefrom which is one-half to twice the diameter of the guide tube, the height of each guide tube being 3 to 10 times the diameter of the guide tube, the lower end of each guide tube being approximately level with the lower end or disposed up to three guide tube diameters above the lower end of the return pipe, and the feedstock to be hydrogenated and the catalyst dispersion are fed above the nozzles for feeding hydrogen.

2. A process according to claim 1 wherein the feedstock to be hydrogenated is fed on a level within a range between about one-half guide tube diameter below the lower end of a guide tube and about one guide tube diameter above the lower end of a guide tube and the feedstock is distributed to several guide tubes.

3. A process according to claim 1 wherein the nozzles for feeding the hydrogen are disposed centrally under respective guide tubes at a distance of one-half to two guide tube diameters.

4. A process according to claim 1 wherein the catalyst is fed to a guide tube.

* * * * *